(12) United States Patent  
Clark (10) Patent No.: US 11,878,126 B2  
(45) Date of Patent: Jan. 23, 2024

(54) MOOD SENSING SHARING DEVICE BASED SYSTEM AND INTERVENTION FOR SYMPTOMS OF STRESS

(71) Applicant: Anthony L. Clark, Saratoga, CA (US)

(72) Inventor: Anthony L. Clark, Saratoga, CA (US)

( * ) Notice: Subject to any disclaimer, the term of this patent is extended or adjusted under 35 U.S.C. 154(b) by 185 days.

(21) Appl. No.: 17/468,653

(22) Filed: Sep. 7, 2021

(65) Prior Publication Data

US 2023/0076131 A1   Mar. 9, 2023

(51) Int. Cl.
*A61M 21/02* (2006.01)
*A61B 5/16* (2006.01)
*A61B 5/00* (2006.01)
*H04W 76/10* (2018.01)
*H04W 4/80* (2018.01)
*G01K 11/12* (2021.01)

(52) U.S. Cl.
CPC ........... *A61M 21/02* (2013.01); *A61B 5/0002* (2013.01); *A61B 5/165* (2013.01); *A61B 5/6826* (2013.01); *A61B 5/742* (2013.01); *H04W 76/10* (2018.02); *G01K 11/12* (2013.01); *H04W 4/80* (2018.02)

(58) Field of Classification Search
CPC ..... A61B 5/0002; A61B 5/165; A61B 5/6826; A61B 5/742; A61M 21/02
See application file for complete search history.

(56) References Cited

U.S. PATENT DOCUMENTS

| 3,802,945 A * | 4/1974 | James ................... B44F 1/14 40/448 |
| 9,064,390 B1* | 6/2015 | Clark .................... G08B 5/36 |
| 9,861,314 B2* | 1/2018 | Haverinen ........... A61B 5/6801 |
| 10,834,535 B2* | 11/2020 | Laakkonen .............. A61B 5/06 |
| 2011/0245633 A1* | 10/2011 | Goldberg ............... A61B 5/165 600/323 |
| 2014/0073486 A1* | 3/2014 | Ahmed ................. A61B 5/684 600/479 |
| 2015/0220109 A1* | 8/2015 | von Badinski ......... H02S 99/00 368/10 |
| 2015/0238140 A1* | 8/2015 | LaBelle ............... A61B 5/0816 600/300 |
| 2016/0066827 A1* | 3/2016 | Workman .............. A61B 5/742 600/340 |
| 2016/0213267 A1* | 7/2016 | Laakkonen ......... A61B 5/02433 |
| 2018/0020937 A1* | 1/2018 | Chou .................... A61B 5/291 600/301 |
| 2018/0042540 A1* | 2/2018 | Kinnunen ........... A61B 5/02433 |
| 2020/0324074 A1* | 10/2020 | Lee ........................ A61B 5/165 |
| 2020/0360651 A1* | 11/2020 | Naddaff ................. A61B 5/486 |
| 2020/0389711 A1* | 12/2020 | Dixit .................. G08B 21/0423 |
| 2020/0397367 A1* | 12/2020 | Kinnunen ........... A61B 5/6801 |
| 2021/0007658 A1* | 1/2021 | Kinnunen ............... A61B 5/11 |

(Continued)

*Primary Examiner* — Joshua T Kennedy (57) ABSTRACT

A mood sensing sharing device (MSSD) powered intervention system, which consists of a smart ring and a paired mobile device is disclosed. The smart ring comprises a mood stone which is configured to display a color that is indicative of a wearer's current emotional state. The smart ring sends current color information for the mood stone to an application on a paired mobile device. The application on the paired mobile device displays one or more guided complementary mitigations (e.g., deep breathing, yoga, meditation, prayer, or other similar relaxation technique) in response to the received mood stone color information.

4 Claims, 7 Drawing Sheets

(56) References Cited

U.S. PATENT DOCUMENTS

| | | | |
|---|---|---|---|
| 2021/0169417 A1* | 6/2021 | Burton | A61B 5/4857 |
| 2021/0204815 A1* | 7/2021 | Koskela | A61B 5/681 |
| 2021/0228942 A1* | 7/2021 | Erkkilä | G16H 50/20 |
| 2021/0233656 A1* | 7/2021 | Tran | A61B 5/7275 |
| 2021/0241649 A1* | 8/2021 | Kinnunen | A61B 5/02055 |
| 2022/0280105 A1* | 9/2022 | Dixit | A61B 5/02405 |
| 2023/0020820 A1 | 1/2023 | Clark | |

\* cited by examiner

Figure 1

Prior Art

Figure 2

Prior Art

Figure 3

Prior Art

Figure 4

Prior Art

Figure 5

Prior Art

Figure 7

MOOD SENSING SHARING DEVICE BASED SYSTEM AND INTERVENTION FOR SYMPTOMS OF STRESS

CROSS-REFERENCE TO RELATED PATENTS AND APPLICATIONS

This application is related to U.S. Pat. No. 9,064,390, titled "System and Method for a Novelty Mood Sensing Sharing Device," awarded Jun. 23, 2015, the entire contents of which are incorporated herein by reference. This application is related to and claims proximity from U.S. Provisional Patent Application No. 63/204,017, titled "A Mood Sensing Sharing Device Based System and Intervention for Symptoms of Stress," filed Sep. 8, 2020, the entire contents of which are incorporated herein by reference. And, this application is related to U.S. patent application Ser. No. 17/372,450, titled "Novel System and Method for the Real-Time, Noninvasive and Continuous In Vivo Sensing of Stress," and filed on Jul. 10, 2021.

STATEMENT REGARDING FEDERALLY SPONSORED RESEARCH OR DEVELOPMENT

Not Applicable.

REFERENCE TO COMPACT DISC APPENDIX

Not Applicable.

BACKGROUND OF THE INVENTION

This invention relates to a novel intervention for a user experiencing emotional distress; utilized Mood Sensing Sharing Device (MSSD) technology to Power a Complementary Treatment ("MPCT"). An example implementation supports a software application guided deep breathing intervention (MSSDBI) session, which is configured to be initiated upon the receipt of certain color information pertaining to a mood on of an attached MSSD jewelry ring. MSSD technology is the subject of U.S. Pat. No. 9,064,390 (Jun. 23, 2015)—"'390 patent." The invention in the '390 patent is a wearable device which communicates the color state of an MSSD's heat sensitive cholesteric stone (i.e., mood stone) to a software application that is comprised in an attached mobile communications apparatus (e.g., smart phone). In contrast to the software application, of the '390 patent's smart phone, which does not implement an intervention or mitigation, the software application of the MPCT invention implements one or more guided complementary mitigations (e.g., deep breathing, yoga, meditation, prayer, or other similar relaxation technique), which are presented in a link, which when selected initiates a specific complementary intervention that is conditioned upon the received MSSD's mood stone color information. Thus, the invention described in this specification combines the mood stone color sharing capabilities of an MSSD per the '390 patent with a complementary intervention to form a novel mood sensing sharing intervention system. An MPCT's mood stone senses and an MPCT's electronic subsystem shares the mood stone's color, indicative of a wearer's emotional state, with an attached smart phone's software application, which then recommends a timelier corresponding mitigation to resolve the symptoms induced by the wearer's emotional state determined by the MPCT's mood stone.

Nervousness is emotional distress which can be triggered by physical or mental events and can be characterized as being ether exogenous or endogenous. A workplace assignment deadline and a school exam are two examples of mental exogenous (i.e., external) events which can increase nervousness. Mental endogenous nervousness inducing events may result from anxiety, depression, or post-traumatic stress disorder (PTSD) for example. Regardless of the origin, nervousness can result in physical symptoms or bodily manifestations. Induced physical symptoms of nervousness or emotional distress include headaches, upset stomach, high blood pressure, chest pain, sexual dysfunction, sleep problems, obesity, anxiety, and depression.

Pharmacology and cognitive behavioral therapy are traditional treatment options for high levels of nervousness or emotional distress, with demonstrated efficacy for the intervention of symptoms. However, cultural and familial considerations may deem these traditional interventions to be prohibitively invasive—which, in turn, may lead to lower compliance, precipitating poorer health outcomes.

Complementary treatment (i.e., intervention) options, such as yoga, meditation, exercise, deep breathing, counting and other relaxation techniques, have been shown to reduce symptoms of high levels of nervousness. Moreover, complementary treatments for emotional distress can be viewed as being more culturally acceptable to some health populations. However, traditional complementary treatments do have some drawbacks. For starters, the required ongoing time commitment to practice may make it difficult to find the time to squeeze such practices into modern oversubscribed schedules. For example, a deep breathing, or a diaphragmatic breathing practice generally entails one or two sessions a day, with each session lasting up to 15 minutes or longer on average. Moreover, the practice of complementary interventions is typically divorced from the event which triggered a particular emotional state. This may make it difficult to maintain a relevancy perspective, which is necessary to maintain compliance. The time lag between the start of a practice and the event which triggered an emotional state, may also make it difficult to link the benefit of a later practice session back to a particular cause. Finally, a delayed use of a practice session may also limit the benefit of the practice. For example, a deep breathing session performed after a migraine headache has ensued may have a limited effect on the practitioner's current pain. In such cases, stronger pharmaceutical treatments may be necessary.

To overcome the aforementioned deficiencies of the existing complementary treatments especially regarding the timeliness of intervention, the MPCT system provides for an alternative, MSSD "alerted" mitigation of the physical symptoms induced by an MPCT wearer's current emotional state. A configurable and intervention identifying mood stone color, when sent by an MSSD, defines the condition whereby a link is presented to a wearer, that when selected initiates a specific complementary intervention. As disclosed in the '390 patent, in the paragraph beginning at column 6 and line 20 regarding a mood stone's color, "the color green is commonly believed to indicate a normal, active emotional state; the color black a tense, nervous emotional state; and the color dark blue a happy, passionate emotional state." Thus, for example, the receipt of black color information by an attached application to an MPCT's MSSD can serve as the triggering event for the start of software guided complementary intervention such as deep breathing. Like other complementary treatments, MPCT is more culturally acceptble compared to traditional pharmaceutical and psychotherapeutic interventions. But, unlike existing traditional and existing complementary treatments, MPCT is less time consuming. Moreover, MPCT is practiced in close time proximity to the casual event-further distinguishing MPCT from traditional and other complementary treatments. And as a consequence, MPCT promises greater compliance, which leads to better health outcomes relative to prior approaches. For example, compared specifically to existing deep breathing interventions for the symptoms of emotional distress, MPCT provides faster acting, timelier interventions that do not require the maintenance of a daily practice.

SUMMARY OF THE INVENTION

The present invention pertains to biofeedback driven, MSSD wearable electronic device the for the complementary intervention of presented symptoms of nervousness. A specific embodiment of MPCT uses a "System and Method for a Novelty Mood Sensing Sharing Device" (in the '390 patent), with the two relevant components of MPCT per the '390 patent being the following: (a) a Smart Ring, comprising a Mood Sensing Sharing Device (MSSD) and (b) a Mood Sensing Sharing App (MSSA).

An MPCT Smart Ring's mood stone's liquid crystal layer is configured such that its entire spectrum of color change indicates a wearer's emotional state, with for example green indicating a normal, active emotional state and black indicating a tense, nervous emotional state. The MPCT Smart Ring's electronic subsystem detects the MPCT Smart Ring's mood stone color and then relays the MPCT Smart Ring's mood stone color information to a paired MPCT MSSA, which then presents a link that when selected initiates a complementary relaxation session, for example, a deep breathing session in the case of an MSSDBI implementation, when the MPCT's mood stone exhibits the color black. Per the '390 patent, the color black is indicative of a "tense, nervous emotional state."

The MPCT Smart Ring and MPCT MSSA recognize symptoms of emotional distress and alert users at the onset of and during earlier stages when conservative intervention can be most effective. Earlier intervention increases the chance of a prompter resolution of induced symptoms.

Emotional distress, induced by anxiety, precipitates physical symptoms, which increase in intensity until a person experiencing the distress becomes aware of their physical discomfort. At that point, the person can begin mitigation (i.e., intervention) steps that ultimately result in the resolution of the symptoms. However, in some instances, long-acting tension may be coincident with delayed awareness, which may make it difficult to pinpoint the origin of the symptoms. If this repeatedly occurs, without addressing the root cause of the distress, a full-blown anxiety disorder may result.

An objective of MPCT is to improve health outcomes regarding symptoms induced by chronic nervousness. In an exemplary implementation, novel adapted breathing sessions, lasting 3-minutes each, are initiated upon notification (i.e., alert) of the onset of a high level of emotional distress. Because awareness and prescriptive mitigation occur sooner, the resolution of induced symptoms can occur more quickly. A second objective of MPCT is to halt the progression in the severity of symptoms before a clinical diagnosis of anxiety disorder or depression is reached. The MPCT powered biofeedback better optimizes the timing of when a complementary intervention is started to mitigate symptoms. This distinguishes MPCT from the prior art whereby the user decides when to initiate a complementary intervention as part of a regular practice. The MPCT biofeedback driven notifications also distinguish MPCT from existing relaxation apps, such as Apple's Breathe App, which randomly generate daily reminders to a user to initiate a relaxation session. Because such reminders are not linked to a particular inducing event, users may find the reminders to be intrusive and unnecessarily disruptive.

DESCRIPTION OF EXEMPLARY EMBODIMENTS

This invention relates to the complementary intervention for symptoms induced by the current emotional disposition of an MPCT wearer. MPCT is a specific embodiment the '390 patent, comprising an MSSD Smart Ring and a modified MESA.

Figure 1:
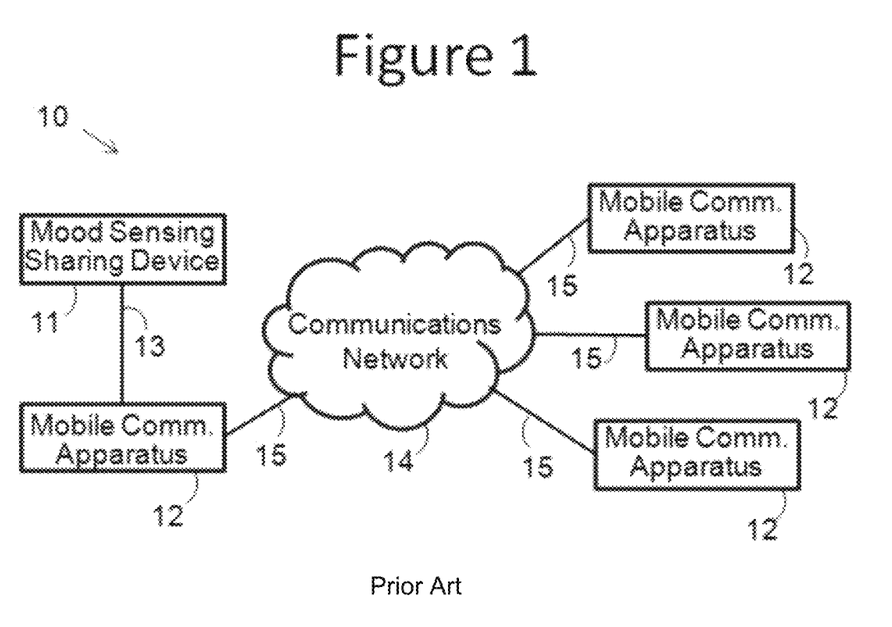
FIG. 1 is FIG. 1 of the '390 patent and is a block level diagram of a mood sensing sharing system.
Figure 5:
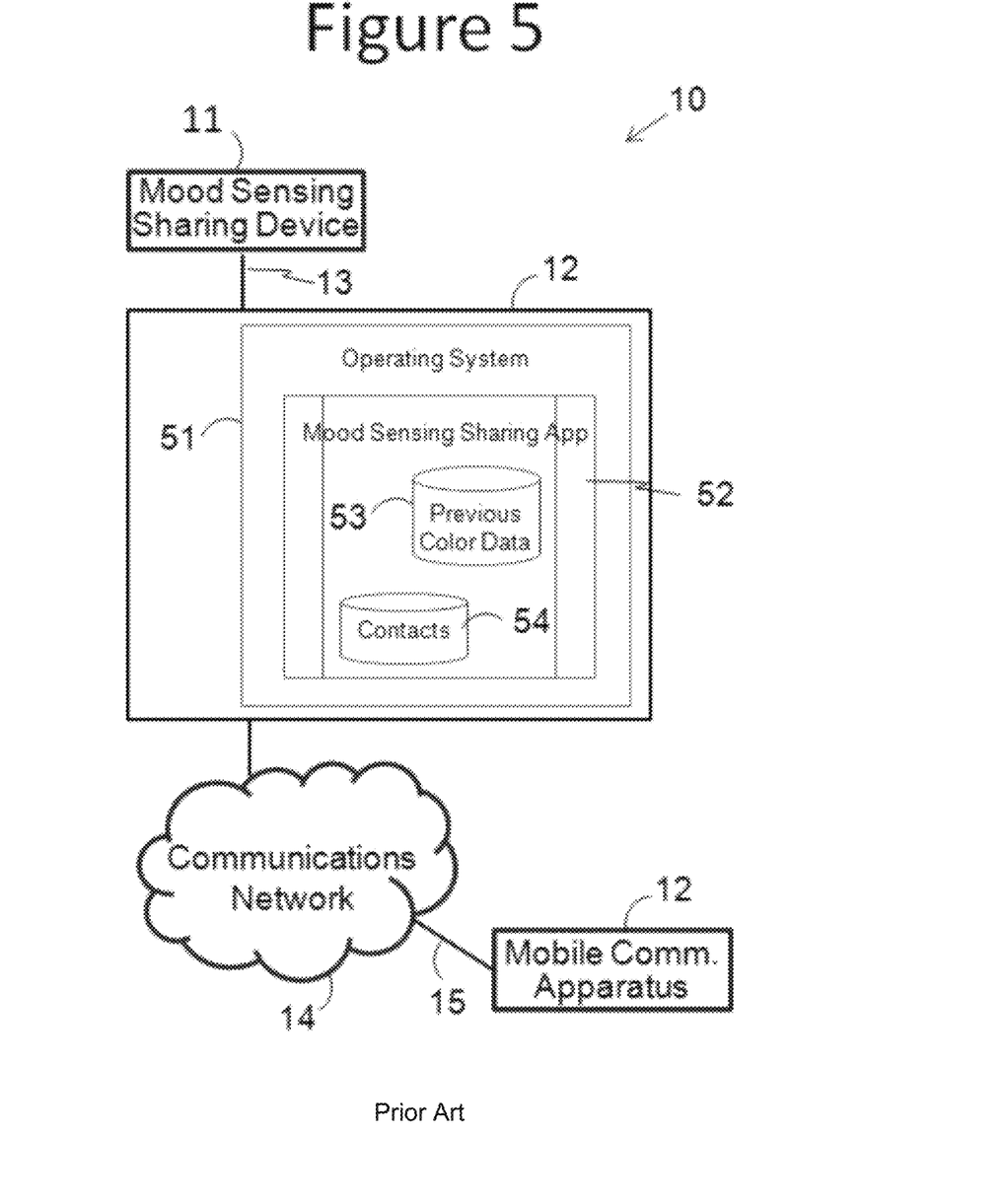
FIG. 5 is FIG. 5 of the '390 patent and illustrates the operating environment and major data structures mood sensing sharing application of a mobile communications apparatus in a mood sensing sharing system.

An MPCT system comprises an MSSD powered Smart Ring 11 and a Mood Sensing Sharing App 52, running on an operating system 51 of a paired mobile communications apparatus 12. In an exemplary embodiment, the mobile communications apparatus (MCA) 12 is an Apple iPhone and the operating system 51 is IOS version 12.x or higher.

Figure 2:
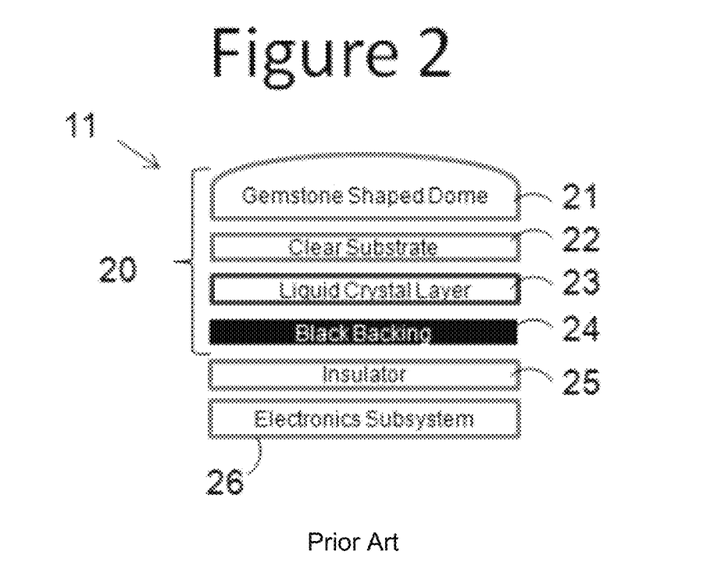
FIG. 2 is FIG. 2 of the '390 patent and is a diagram of one implementation of a partially exploded mood sensing sharing device.
Figure 3:
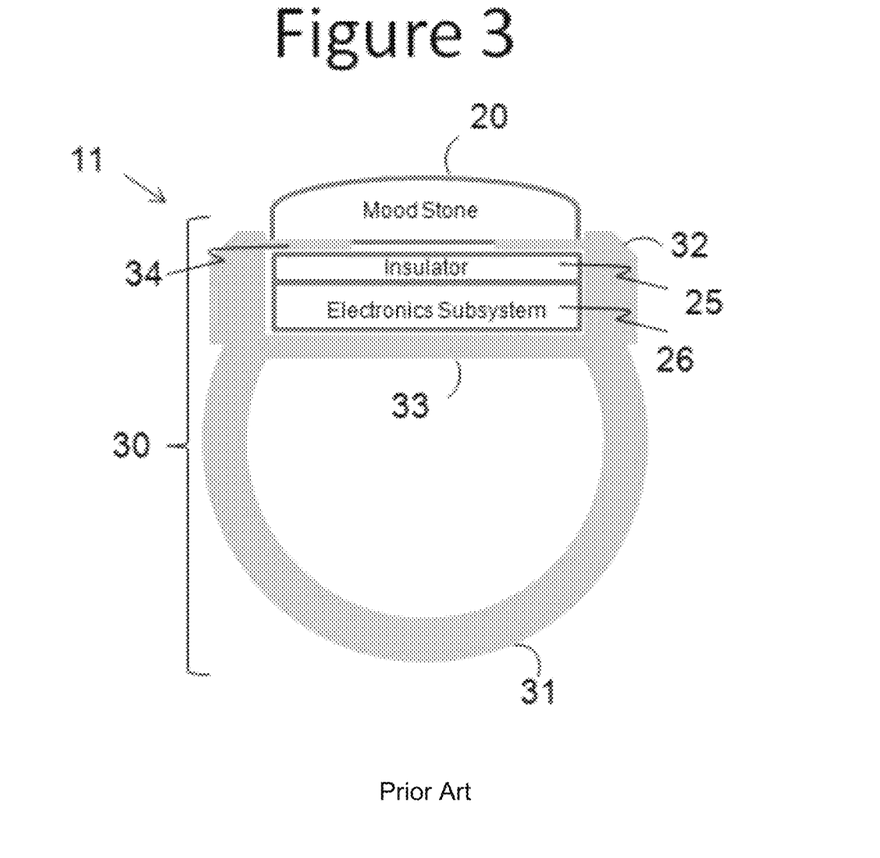
FIG. 3 is FIG. 3 of the '390 patent and is a vertical dross section view of a mood sensing sharing device in the setting of a ring.

An MPCT Smart Ring 11, which is worn on a finger of a wearer, comprises a mood stone and an electronics subsystem (ES)—consisting of one or more biosensors, a microprocessor, memory, wireless, connectivity and a powering—charging element—all housed within a ring chassis.

In an exemplary embodiment, the MPCT Smart Ring's 11 chassis' components 31 and 32 are comprised of a 3D printed carbon fiber material.

In an exemplary embodiment, the mood stone 20 of an MPCT Smart Ring 11 is a decorative Thermochromic Liquid Crystal decorative ring stone. In an exemplary embodiment, the mood stone is as taught in FIG. 2, element and in Table 1 of the '390 patent, inclusive of a clear gemstone shaped acrylic dome 21; a clear polyester plastic sheet 22; a microencapsulated thermochromic liquid crystal ink layer 23; and a black polyester backing layer 24.

Figure 4:
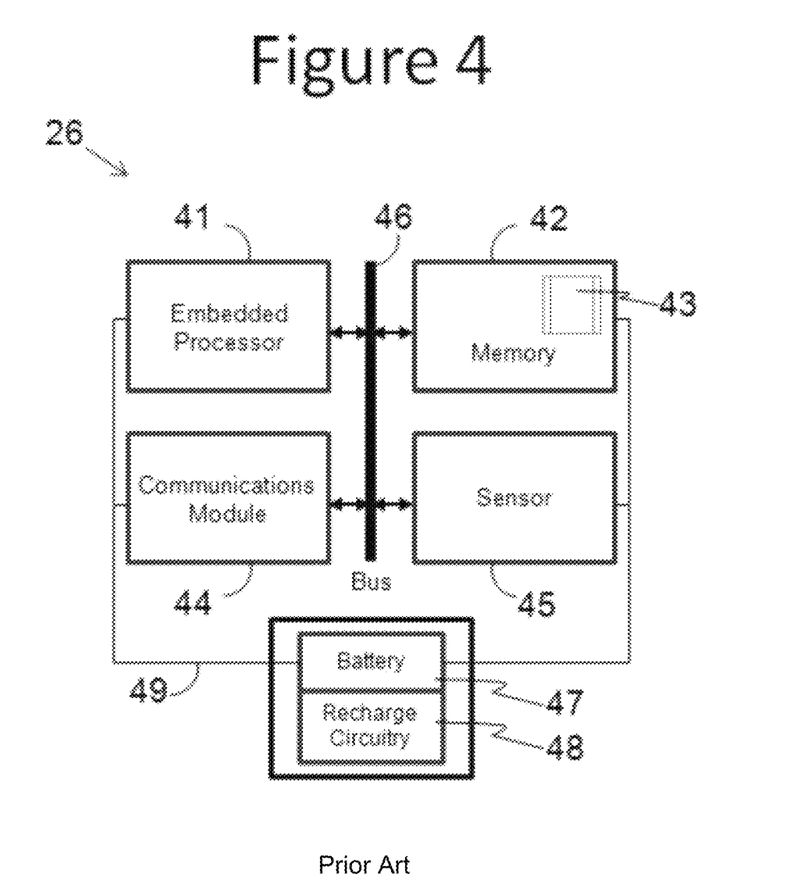
FIG. 4 is FIG. 4 of the '390 patent and is a block diagram of an embodiment of the electronics subsystem of a mood sensing sharing device.

A sensor 45 within an MPCT Smart Ring 11 tracks the color of a mood stone 20, which detects subtle physiological changes in the body, of which research has demonstrated are due to the autonomic nervous system's response to emotion. In an exemplary embodiment the sensor 45 is a programmable, low operating current, digital temperature thermometer having the following characteristics: a minimum range of 20 degrees C. to 40 degrees C.; a minimum resolution of 0.5 degrees C.; a minimum accuracy of 0.5 degrees C.; and a response time of less than 1 second.

An MPCT Smart Ring 11 comprises an electronics subsystem 26. In an exemplary embodiment, the MPCT Smart Ring's 11 electronics subsystem 26 comprises an embedded processor 41, which is a low power, mixed signal 16-bit APM® based micro-controller, having both integrated digital-to-analog and analog-to-digital converters.

In an exemplary embodiment, the MPCT Smart Ring's 11 electronics subsystem's 26 memory 42 is a NAND flash memory module having a density of 256 Megabytes and a having a bus width of 16-bits.

Wireless connectivity is provided by an electronics subsystem's 26 communications module 44 within an MPCT Smart Ring 11 and provides Bluetooth® communication with a paired mobile device MCA 12 running MSSD aware MSSA 52 software. In an exemplary embodiment the Bluetooth Low Energy v4.0 standard protocol is implemented.

The MPCT Smart Ring's 11 electronics subsystem's 26 powering-charging element comprises a battery 47 and recharge circuitry 48. In an exemplary embodiment the battery 47 is a 3.7V LTPO battery, having built-in overcharge protection circuitry, and the recharge circuitry 48 comprises a USB wall charging adaptor with analog circuitry to adapt a wall outlet's AC current into 4V DC charging current.

The MPCT deep breathing Intervention is a software routine within an MSSA 52 (MSSDBI). An MSSDBI receives mood stone color information pertaining to the current physiological state of a wearer by the wearer's paired MPCT Smart Ring 11 via a Bluetooth connection per communications module 44. In an exemplary embodiment, the mood stone's 20 color information, for an MPCT Smart Ring 11, is mapped via a software algorithm to a wearer's current mood level: corresponding to a particular mood stone color range "Blue," "Green," "Red," and "Black." In an exemplary embodiment, a mood stone's 20 color of "Black" is indicative of a wearer of an MPCT Smart Ring 11 experiencing elevated levels of tension or emotional distress.

Figure 6:
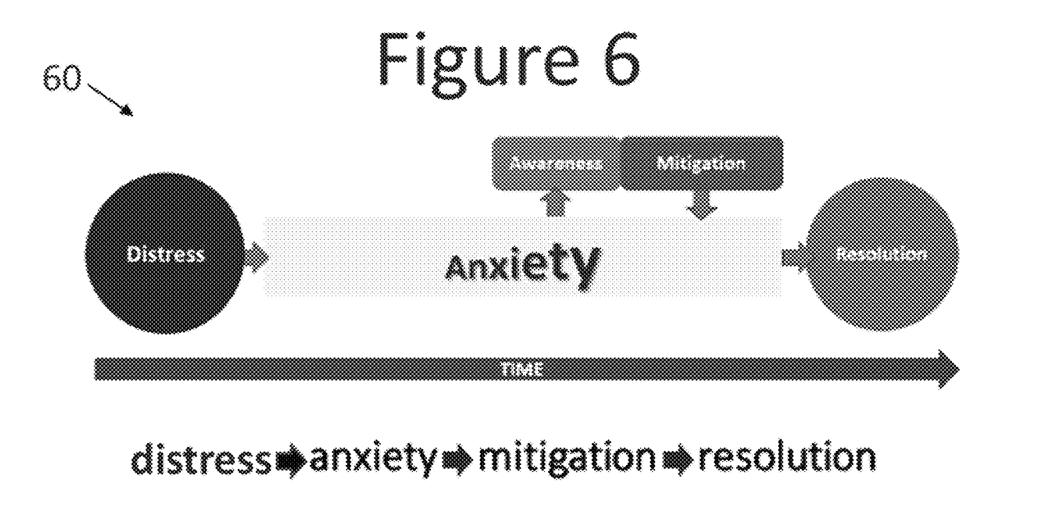
FIG. 6 is a model showing the delayed progression and delayed resolution of symptoms induced by emotional distress.
Figure 7:
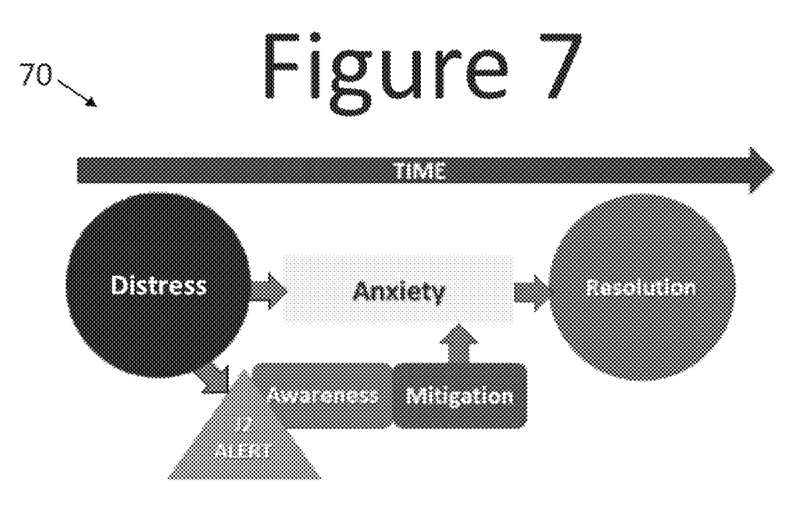
FIG. 7 is a model showing the operation of MPCT, resulting in the quicker mitigation and quicker resolution of emotional distress induced symptoms.

In an exemplary embodiment, the liquid crystal layer 23 of an MPCT Smart Ring's 11 mood stone 20 is configured such that its entire spectrum of color change indicates a wearer's emotional state, with green corresponding to a normal, active emotional state, dark blue corresponding to happy, passionate emotional state, and black corresponding to a tense, nervous emotional state. The MPCT Smart Ring's 11 electronic subsystem 26 detects the MPCT Smart Ring's 11 mood stone 20 color and then sends the MPCT Smart Ring's 11 mood stone 20 color information to a paired MPCT MSSA 52, which echoes the mood stone's 20 color and compares the received mood stone's 20 color to a configurable and complementary intervention specific color, which for this exemplary embodiment is the color black. When the MPCT MSSA 52 receives mood stone 20 color information indicating the color black—corresponding to a tense, nervous emotional state—and when the MPCT MSSA 52 is in the foreground of the operating system's 51 user interface, the MPCT MSSA 52 concurrently, along with the echoed mood stone 20 color, presents the wearer of the MPCT Smart Ring with a link, which when selected initiates an embedded deep breathing module within the MSSDBI capable MPCT MSSA 52. This facilitates the timelier intervention of induced symptoms of high levels of emotional distress as illustrated in FIG. 6 and FIG. 7. Expedited awareness and quicker mitigation in FIG. 2 leads to the quicker resolution of symptoms caused by emotional distress.

In the exemplary embodiment immediately above, but when the MSSDBI capable MSSA 32 is in the background of the operating system's 51 user interface, system notifications alert the wearer and present a link to access an embedded deep breathing module within the MSSA 52.

In an exemplary embodiment, the deep breathing module within an MSSDBI example MPCT MSSA 52 guides a wearer through a 3 minutes long breathing session, intended to intervene the wearer's experience of physical symptoms arising from high levels of nervousness or emotional distress.

While in the foregoing, there have been described specific apparatuses and methods for the present invention, it is to be clearly understood that the provided description is exemplary and is not to limit the scope of invention.

I claim:

1. A mood sensing sharing intervention system, for sensing emotions and for displaying a complementary intervention for the quicker resolution of induced physical symptoms of emotion, comprising:
   a smart ring, which is worn by a wearer on a finger, and
   a paired mobile communications apparatus,
      wherein the smart ring is a mood sensing sharing device comprising a mood stone and an electronics subsystem, said mood stone configured to display a color which is indicative of the wearer's current emotional state, said electronics subsystem configured to detect the mood stone's color, and said electronics subsystem configured to share current mood stone color information with the paired mobile communications apparatus; and
      wherein the paired mobile communications apparatus comprises a mood sensing sharing app, said mood sensing sharing app configured to receive mood stone color information from the smart ring and configured to display a link, which when selected initiates a complementary intervention based on the received mood stone color information.

2. The mood sensing sharing intervention system of claim 1, wherein the mood stone comprises a liquid crystal layer that is configured to turn black when the wearer of the smart ring is experiencing a tense, nervous emotional state.

3. The mood sensing sharing intervention system of claim 1, wherein the complementary intervention is a software guided 3-minutes long deep breathing session, which is initiated upon the selection of a link, said link presented upon the receipt of mood stone color information which indicates the color black.

4. A mood sensing sharing intervention system comprising:
   a smart ring, which is configured to be worn by a wearer on a finger and which comprises a mood stone and an electronics subsystem, said mood stone configured to display a color which is indicative of the wearer's current emotional state, said electronics subsystem configured to detect the mood stone's color, and said electronics subsystem configured to share current mood stone color information over a wireless connection; and
   a paired mobile communications apparatus, which comprises a mood sensing sharing app, said mood sensing sharing app configured to receive mood stone color information from the smart ring over the wireless connection and said mood sensing sharing app configured to display a link, which when selected initiates a complementary intervention, based on the mood stone color information received by said mood sensing sharing app.

\* \* \* \* \*